US00PP16216P2

(12) United States Plant Patent
Speichert

(10) Patent No.: US PP16,216 P2
(45) Date of Patent: Jan. 24, 2006

(54) *ACORUS* PLANT NAMED 'GOLDEN PHEASANT'

(50) Latin Name: *Acorus gramineus*
Varietal Denomination: Golden Pheasant

(76) Inventor: C. Greg Speichert, 11717 Monroe Pl., Crown Point, IN (US) 46307

( * ) Notice: Subject to any disclaimer, the term of this patent is extended or adjusted under 35 U.S.C. 154(b) by 88 days.

(21) Appl. No.: 10/987,264

(22) Filed: Nov. 12, 2004

(51) Int. Cl.
*A01H 5/00* (2006.01)

(52) U.S. Cl. ..... Plt./342
(58) Field of Classification Search ..... Plt./342
See application file for complete search history.

*Primary Examiner*—Anne Marie Grunberg
(74) *Attorney, Agent, or Firm*—Penny J. Aguirre

(57) ABSTRACT

A new cultivar of *Acorus gramineus,* 'Golden Pheasant', characterized by its chartreuse to golden colored foliage on plants that reach a height of about 12 to 14 inches.

2 Drawing Sheets

Botanical classification: *Acorus gramineus.*
Varietal denomination: 'Golden Pheasant'.

BACKGROUND OF THE INVENTION

The present invention relates to a new and distinct cultivar of *Acorus gramineus* and will be referred to hereafter by its cultivar name, 'Golden Pheasant'. 'Golden Pheasant' is a new cultivar Japanese sweet flag, a perennial ornamental grass grown for landscape use.

The inventor discovered the new cultivar, 'Golden Pheasant' in October of 2000 as a whole fan sport of *Acorus gramineus* 'Yodonoyuki' (not patented) in a cultivated area of his nursery in Cedar Lake, Ind.

The new cultivar 'Golden Pheasant' was selected for its unique golden foliage. The parent plant, 'Yodonoyuki', has green foliage dusted with tints of gold. The foliage of 'Golden Pheasant' ranges in color from chartreuse to gold. The closest comparison plant to 'Golden Pheasant' is *Acorus gramineus* 'Pusillus aurea' (Not patented), a cultivar with golden foliage but with a dwarf stature, reaching only 3 inches in height, whereas 'Golden Pheasant' grows to about 12 inches in height. *Acorus gramineus* 'Ogon' (Not patented) differs from 'Golden Pheasant' in that the foliage has gold and green variegation.

Asexual reproduction of the new cultivar was first accomplished by rhizome division in Cedar Lake, Ind. in November of 2000 by the inventor. The characteristics of this cultivar have been determined to be stable and are reproduced true to type in successive generations.

SUMMARY OF THE INVENTION

The following traits have been repeatedly observed and represent the characteristics of the new *Acorus.* 'Golden Pheasant' has not been observed under all possible environmental conditions. The phenotype may vary somewhat with variations in temperature, day-length, light intensity, soil types, and water and fertility levels without, however, any variance in genotype. The general observations, and descriptions that follow describe plants that were grown outdoors in a trial bed in Cedar Lake, Ind. for a period of three years. These attributes in combination distinguish 'Golden Pheasant' from all other selections of *Acorus* known to the inventors.

1. The foliage of 'Golden Pheasant' is golden in color; the color of new foliage emerges chartreuse with the mature leaves becoming more golden to light yellow as the season progresses.
2. 'Golden Pheasant' reached a height of about 30 to 35 cm (12 to 14 inches) and a spread of 30 to 60 cm (12 to 24 inches).
3. 'Golden Pheasant' is readily propagated by rhizome division.

BRIEF DESCRIPTION OF THE DRAWING

The accompanying colored photographs illustrate the overall appearance and distinct characteristics of the new *Acorus* as grown in 2-gallon containers in Zeeland, Mich.

The photograph in FIG. 1 was taken in early summer and illustrates the overall habit and color of the mature foliage of 'Golden Pheasant'.

Figure 1:
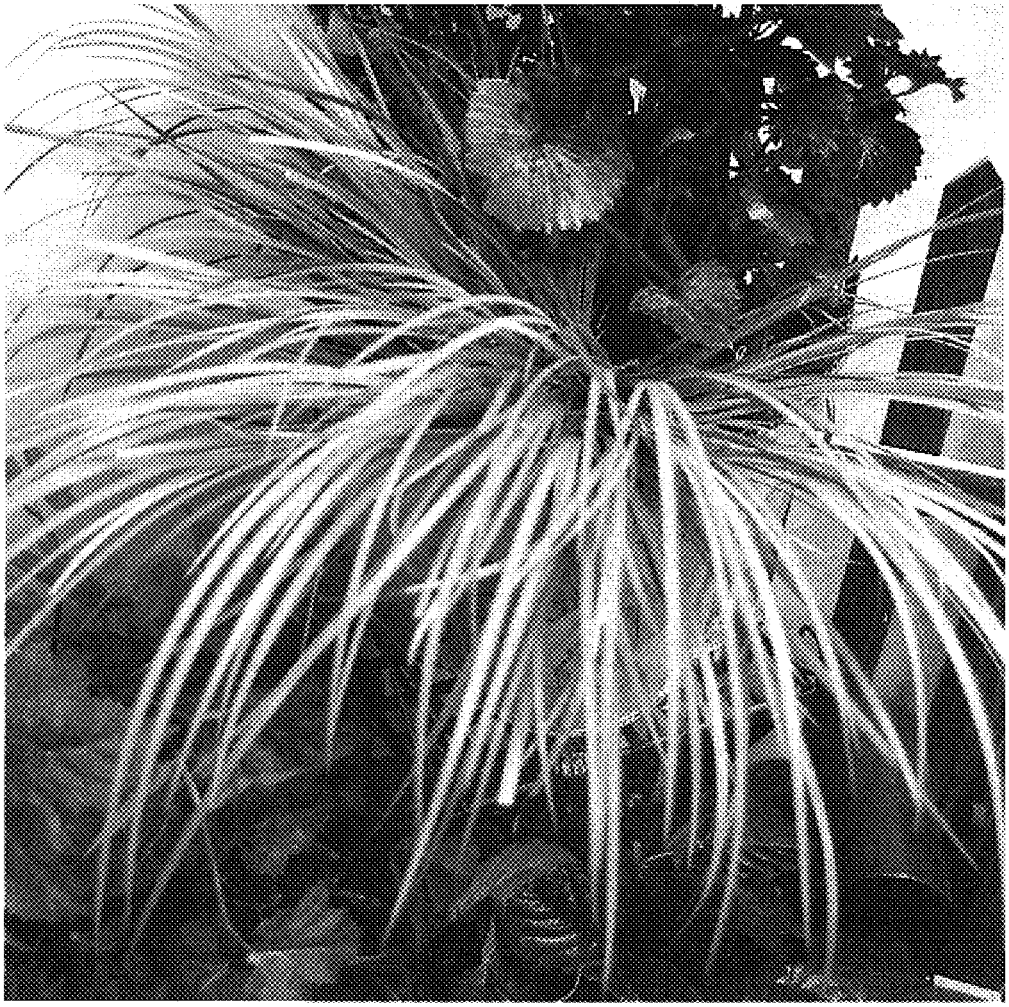
Figure 2:
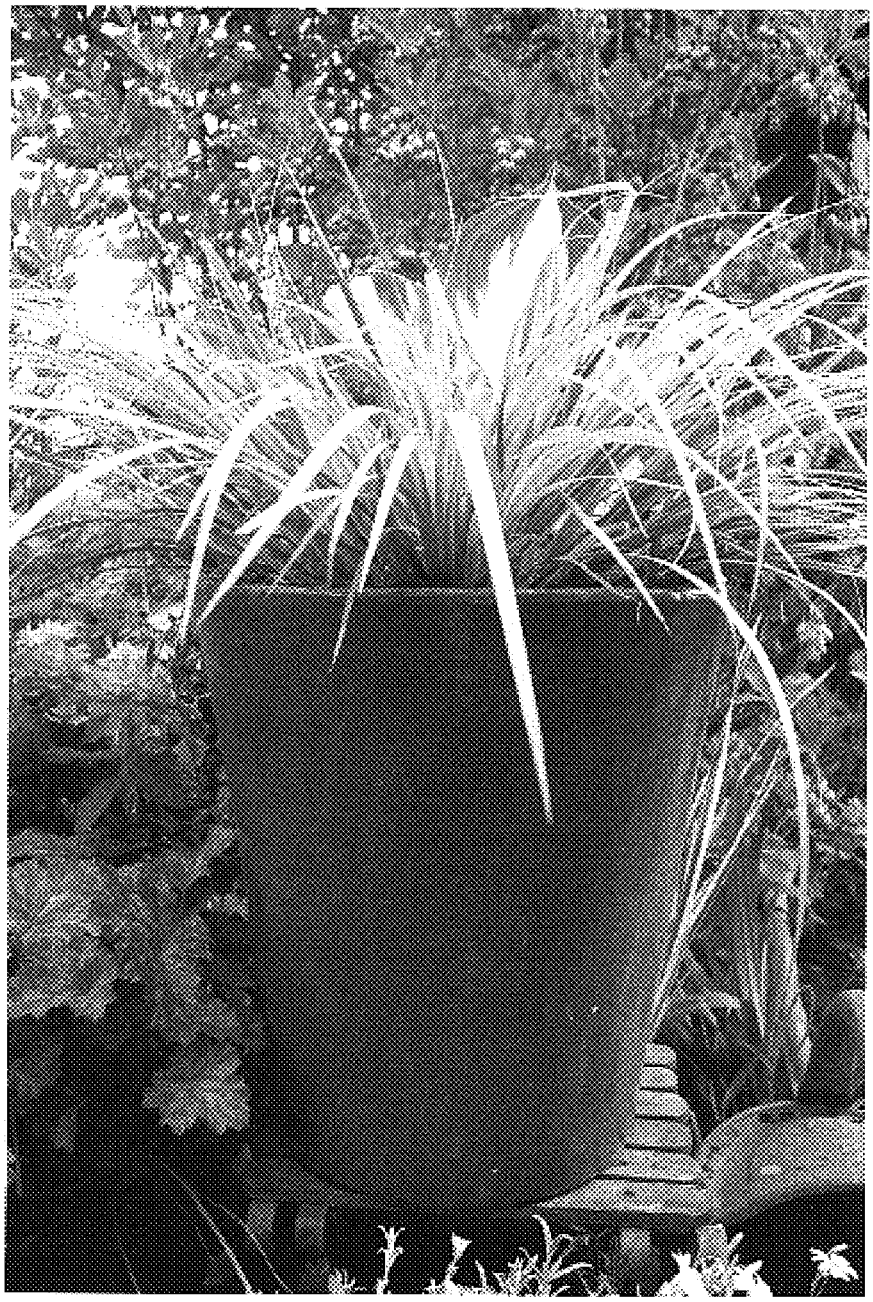

The photograph on FIG. 2 was taken in early summer and illustrates the foliage color of 'Golden Pheasant' early in the season.

The colors in the photographs are as close as possible with the photographic and printing technology utilized and the color values cited in the detailed botanical description accurately describe the colors of the new *Acorus.*

DETAILED BOTANICAL DESCRIPTION

The general observations and descriptions describe plants that were grown outdoors in a trial bed in Cedar Lake, Mich. for three years. The color determinations are in accordance with the 2001 R.H.S. Colour Chart of The Royal Horticultural Society, London, England, except where general color terms of ordinary dictionary significance are used.

Botanical classification: 'Golden Pheasant' is a cultivar of *Acorus gramineus.*
Parentage: Whole fan sport of *Acorus gramineus* 'Yodonoyuki'.
General description:
*Plant habit.*—Herbaceous, slowly spreading from compact rhizomes in circular growth pattern, ornamental grass, non-invasive.

*Height and spread.*—Reaches about 30 to 35 cm (12 to 14 inches) in height and a spread of 30 to 60 cm (12 to 24 inches), a division 9 cm in diameter has an average of 6 rhizomes.

*Cold hardiness.*—USDA Zone 5.

*Culture.*—Grows best in part shade in fertile, moist soils in full sun to light shade.

*Diseases and pests.*—No evidence of rust has been observed in trials.

*Root description.*—Rhizomes with wiry roots, rhizomes are about 2 cm in length and about 0.75 cm in width at leaf attachment, and 155B in color with ridges from prior leaf attachment that are N199B in color.

Growth and propagation:

*Propagation.*—Rhizome division.

*Time required for root development.*—About 12 to 15 weeks is required to finish in a 2½ inch container from a single rhizome when grown in a greenhouse during the summer months under ambient temperatures in Zeeland, Mich. If grown in cooler months, night temperatures should be kept above 60° F. for root development to occur. Shade cloth during summer months intensifies foliage coloration.

Foliage description:

*Leaf shape.*—Linear.

*Leaf division.*—Simple.

*Leaf base.*—Sheathed to rhizome.

*Leaf apex.*—Acute, attenuating to a point at apex.

*Leaf margin.*—Entire.

*Leaf aspect.*—Leaves initially emerge upright, then cascade downward.

*Leaf venation.*—Parallel, not prominent or conspicuous, 144A in color on both surfaces.

*Leaf persistence.*—Dry to a brown color, 165D, but remain are persistent through winter.

*Leaf fragrance.*—Sweet.

*Leaf attachment.*—Sheathed to rhizome.

*Leaf size.*—Up to about 0.5 cm in width and up to about 30 cm in length.

*Leaf number.*—About 8 to 10 leaves per rhizome by mid September.

*Leaf arrangement.*—Equitant (overlapping), emerge from center, sheathed to base.

*Leaf surface.*—Glabrous on upper and lower surface.

*Leaf color.*—Upper and lower surfaces: emerging leaf color; N144A to N144B (yellow-green), mid season leaf color; base of 144A (yellow-green) with primary leaf color of 153D (yellow-green but more golden), late season leaf color; base of 144B (yellow-green) with primary leaf color of 14D (yellow-orange).

Flower and seed description: Flowering has not been observed for 'Golden Pheasant' under the conditions tested. *Acorus gramineus* generally has insignificant blooms and bloom only when grown in water, such as a pond.

I claim:

1. A new and distinct cultivar of *Acorus* plant named 'Golden Pheasant' as herein illustrated and described.

* * * * *